Figure 1:
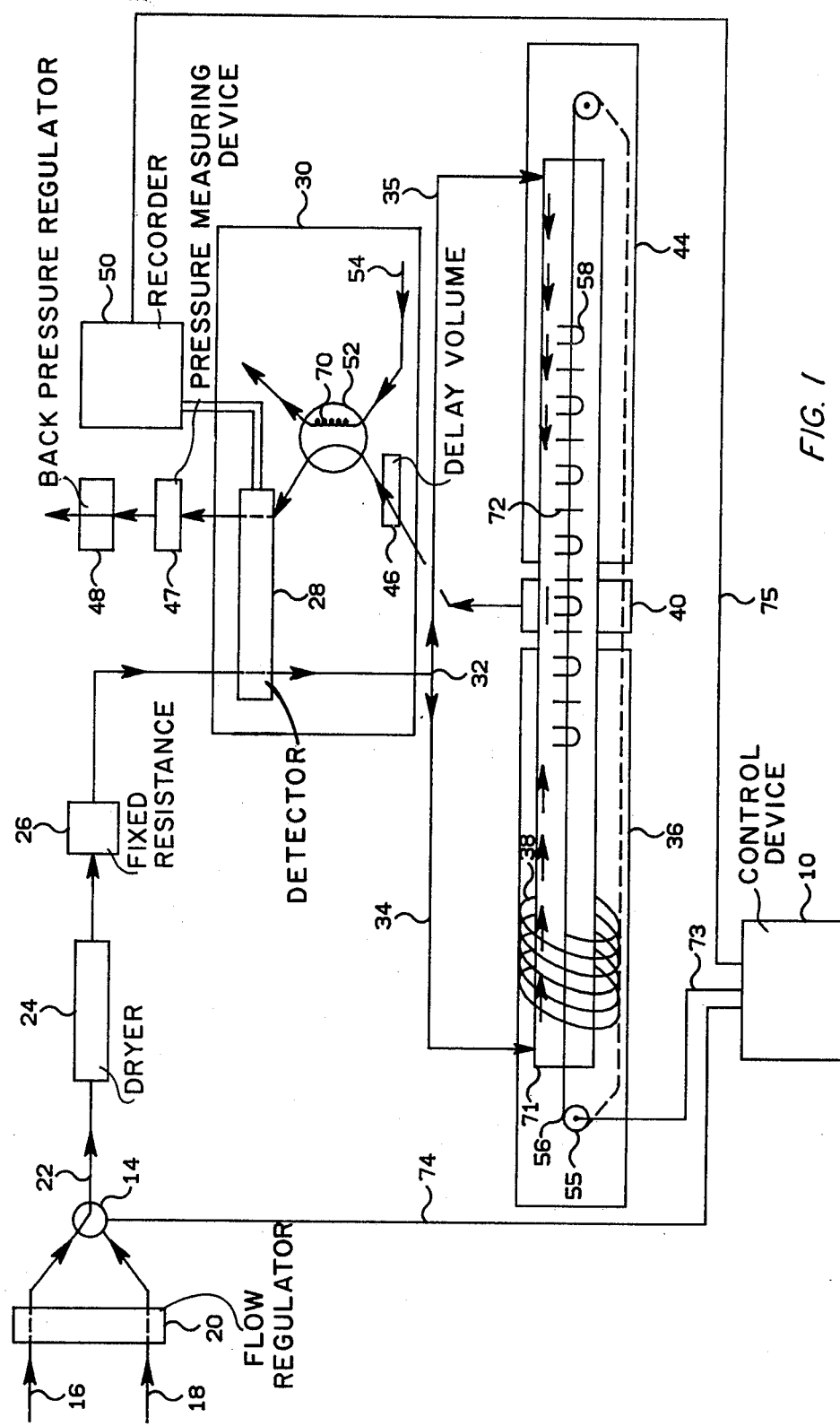

United States Patent [19]

Scott

[11] 4,450,723

[45] May 29, 1984

[54] MULTI-SAMPLE SURFACE AREA MEASUREMENT

[75] Inventor: Richard L. Scott, Bartlesville, Okla.

[73] Assignee: Phillips Petroleum Company, Bartlesville, Okla.

[21] Appl. No.: 358,743

[22] Filed: Mar. 16, 1982

Related U.S. Application Data

[63] Continuation-in-part of Ser. No. 128,981, Mar. 10, 1980, Pat. No. 4,335,610.

[51] Int. Cl.³ ............................................. G01N 15/02
[52] U.S. Cl. ................................................. 73/432 PS
[58] Field of Search .............................. 73/432 PS, 38

[56] References Cited

U.S. PATENT DOCUMENTS

| | | | |
|---|---|---|---|
| 2,692,497 | 10/1954 | Van Nordstrand | 73/432 PS X |
| 2,729,969 | 1/1956 | Innes | 73/432 PS X |
| 2,960,870 | 11/1960 | Nelsen et al. | 73/432 PS |
| 3,059,478 | 10/1962 | Coggeshall et al. | 73/432 PS |
| 3,203,252 | 8/1965 | Polinski et al. | 73/432 PS |
| 3,211,006 | 10/1965 | Haley, Jr. | 73/432 PS |
| 3,211,007 | 10/1965 | Atkins | 73/432 PS |
| 3,222,133 | 12/1965 | Ballou et al. | 73/432 PS X |
| 3,255,122 | 6/1966 | Constabaris et al. | 73/432 PS X |
| 3,262,319 | 7/1966 | Orr, Jr. et al. | 73/432 PS |
| 3,295,720 | 1/1967 | Slone | 73/432 PS X |
| 3,296,869 | 1/1967 | Bultemann | 73/432 PS |
| 3,299,713 | 1/1967 | Haul et al. | 73/432 PS |
| 3,306,112 | 2/1967 | Jenckel | 73/432 PS |
| 3,349,625 | 10/1967 | Benusa et al. | 73/432 PS |
| 3,464,273 | 9/1969 | Hendrix et al. | 73/432 PS |
| 3,482,452 | 12/1969 | Tabikh | 73/432 PS |
| 3,500,675 | 3/1970 | Sandstede et al. | 73/432 PS X |
| 3,509,762 | 5/1970 | Conway et al. | 73/104 |
| 3,555,912 | 1/1971 | Lowell | 73/432 PS |
| 3,707,870 | 1/1973 | Herve et al. | 73/38 |
| 3,732,736 | 5/1973 | Glaude et al. | 73/432 PS |
| 3,771,367 | 11/1973 | Lowell et al. | 73/432 PS |
| 3,783,697 | 1/1974 | Lowell et al. | 73/432 PS |
| 3,850,040 | 11/1974 | Orr, Jr. et al. | 73/432 PS |
| 3,884,083 | 5/1975 | Lowell | 73/432 PS |

FOREIGN PATENT DOCUMENTS 1129734  5/1962  Fed. Rep. of Germany ... 73/432 PS

Primary Examiner—Gerald Goldberg
Assistant Examiner—Joseph W. Roskos

[57] ABSTRACT

The surface area of a plurality of samples is measured in an apparatus in which these samples are all included in a housing, subjected to adsorption of the adsorbing fluid and seriatim moved into a desorption zone in which one sample at a time is subjected to a desorption step. In another embodiment, a plurality of individual sample holders are each provided with an individual heating element to allow seriatim desorption by switching the heating of the samples from one heating element to the next. No movement of the sample holders is required in this embodiment. The apparatus and operation lends itself to automation.

7 Claims, 5 Drawing Figures

MULTI-SAMPLE SURFACE AREA MEASUREMENT

This application is a continuation-in-part of Ser. No. 128,981, filed Mar. 10, 1980, now U.S. Pat. No. 4,335,610.

The present invention relates to an apparatus and a process for measuring the surface area of each of a plurality of samples. More specifically, the present invention relates to an apparatus and a process for carrying out surface area measurements on a plurality of samples in an automatized way.

BACKGROUND OF THE INVENTION

The surface area of materials is a property of great significance in several applications. Silica-alumina and carbon black are two examples of products where one of the important characteristics is the surface area. In several catalytically promoted reactions, the surface area of the catalyst determines not only the yield of the process, but in several instances, the reaction result and the chemical composition of the product made.

In view of the importance of the surface area, methods have been developed for an accurate determination thereof. One known method consists in contacting a weighed sample, the surface area of which is to be determined, with fluid which is adsorbed onto the surface area of the sample. The larger the surface area of the samples of the same weight will be, the larger the quantity of adsorbed fluid on such a sample will be. The so pretreated sample is then subjected to heat to effect desorption of the adsorbed fluid into a carrier gas stream. The carrier gas stream containing the desorbed adsorbing fluid is passed through a detector from which the amount of adsorbing fluid that has been desorbed from the samples in the carrier gas is measured, displayed, registered. Thereby the total quantity of desorbed adsorbing fluid can be determined and the surface area of the sample can be determined.

Whereas the process described is very accurate and effective, it is also a time consuming and labor intensive procedure. It would be desirable to have an apparatus and method available which allow the measurement of a multitude of samples and which lend themselves to automatic operation.

Therefore, it is one object of this invention to provide an apparatus for measuring the amount of a fluid desorbed from a plurality of samples. Another object of this invention is to provide a process for measuring the quantity of an adsorbing fluid desorbed on each of a plurality of samples without having to complete each and every step of the measurement on one sample before the next sample can be handled, but still using only one detecting device.

A further object of this invention is to provide means for automatic measurement of the surface area of a plurality of samples.

Figure 2:
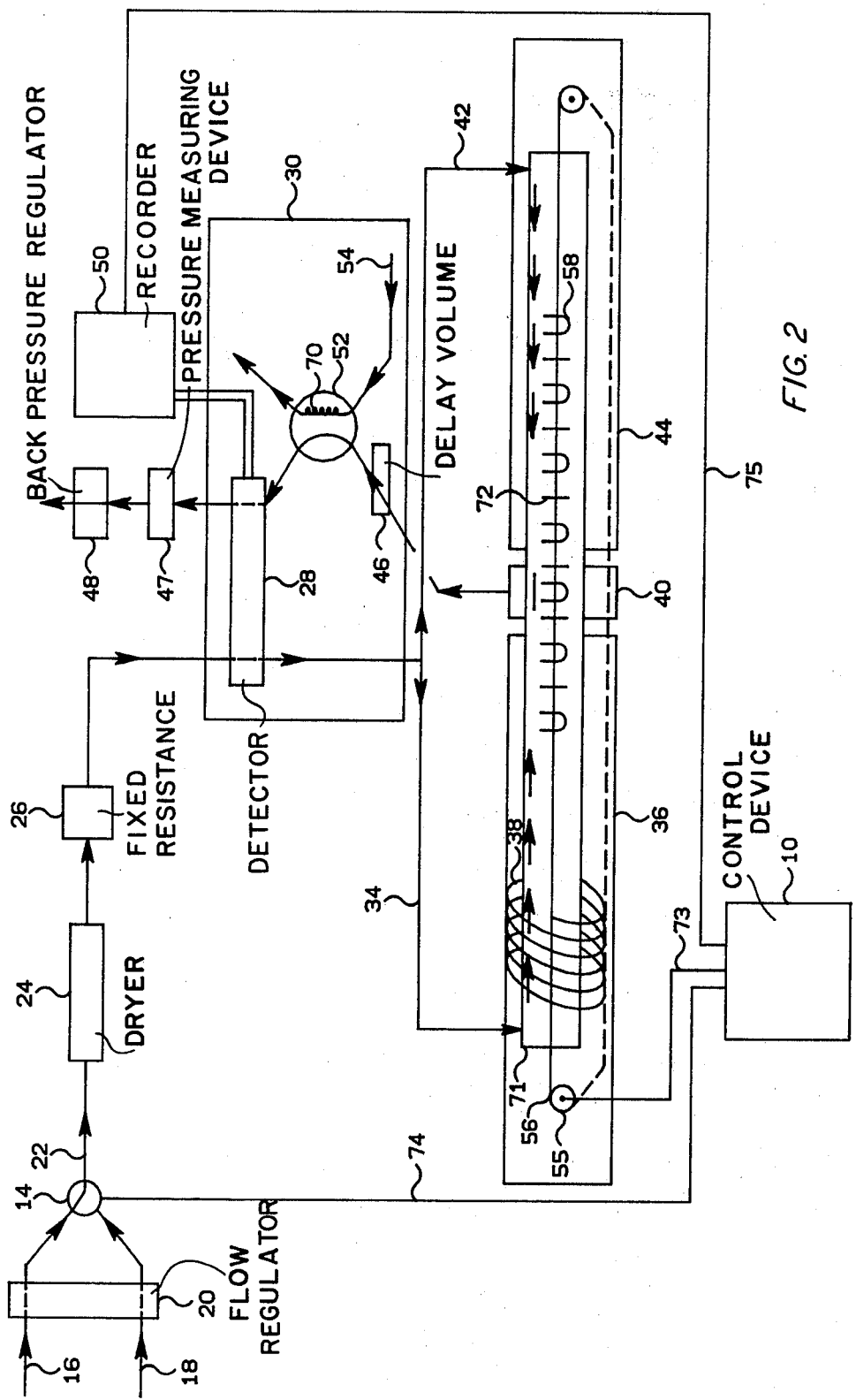
Figure 3:
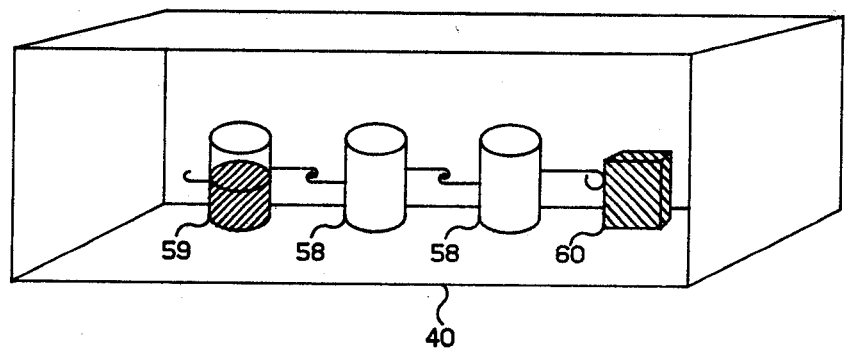
Figure 4:
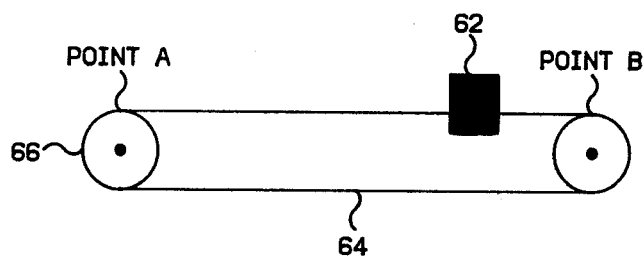
Figure 5:
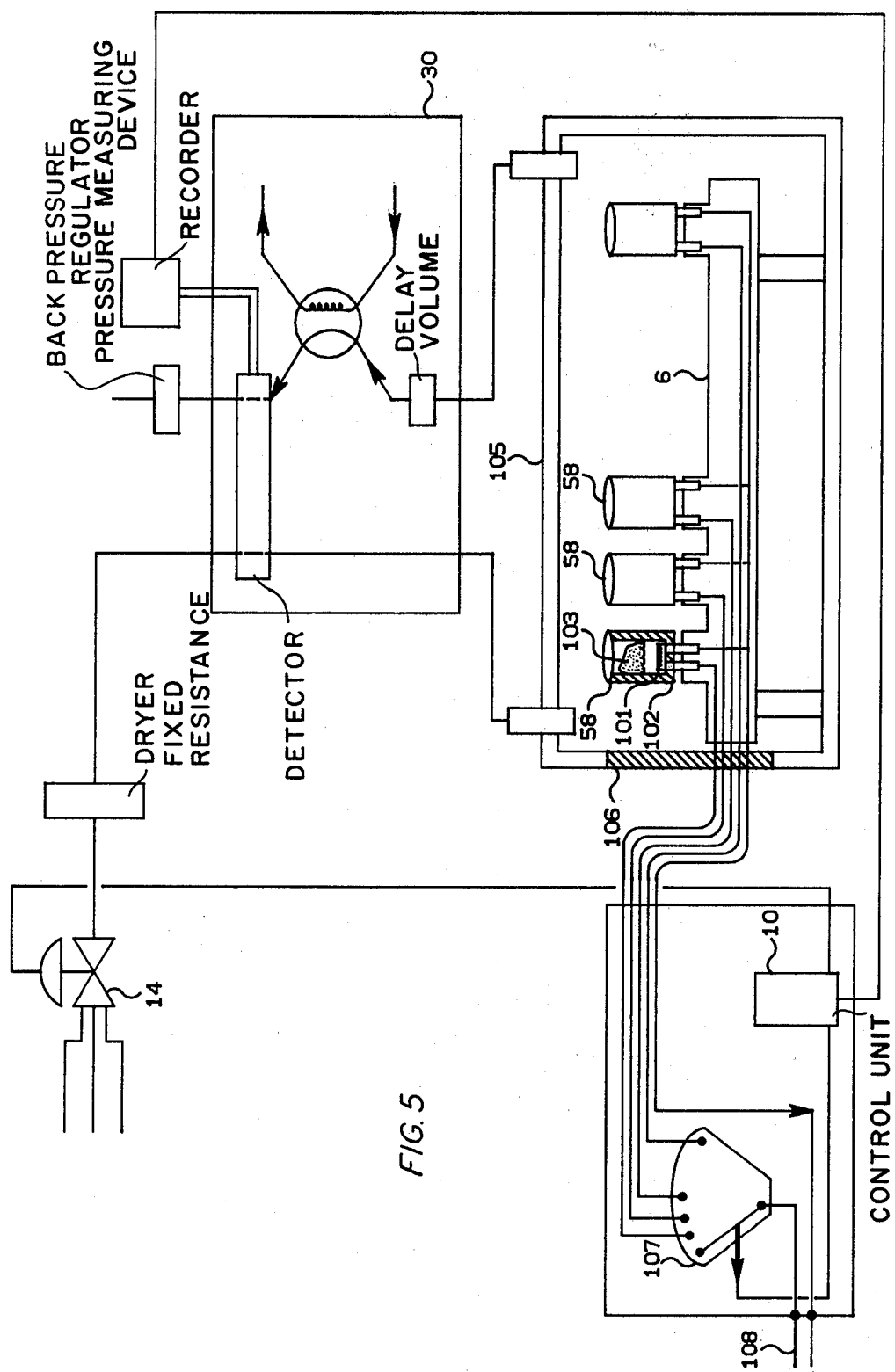

These and other objects, advantages, details, features and embodiments of this invention will become apparent to those skilled in the art from the following detailed description of the invention, the appended claims and the drawing in which FIG. 1 is a schematic representation of an apparatus of this invention for measuring surface areas of a plurality of samples, FIG. 2 shows another embodiment of this invention with one gas inlet to the housing and one gas outlet from the housing, FIG. 3 represents a schematic perspective view of a sample holder train with a pulling magnet, FIG. 4 is a schematic representation of a mechanism for moving the sample supports through the various zones of this apparatus, and FIG. 5 shows another embodiment of this invention wherein a separately activated heating element is provided for each of a plurality of stationary sample holders.

STATEMENT OF THE INVENTION

In accordance with this invention, an apparatus for measuring the amount of fluid adsorbed by a plurality of samples is provided. This apparatus comprises an adsorption zone and a desorption zone thermally insulated from each other in a housing. The adsorption zone is provided with means for exposing the samples to the fluid to be adsorbed, whereas the desorption zone is provided with means for causing the release of at least some of the fluid adsorbed from the sample. A detector is operatively connected to the desorption zone so that the quantity of fluid released from a sample can be determined. Transporting means are operatively associated with the adsorption and desorption zone to allow the transportation of the samples from the adsorption zone to the desorption zone. Preferably, the apparatus also comprises a drying zone within the housing so that the plurality of samples can be all first subjected to drying thereafter to adsorption and thereafter seriatim to desorption and measurement of the surface area.

Another embodiment of this invention resides in a process for determining the quantity of a fluid adsorbed by each of a plurality of samples. This process comprises the steps of adsorbing, desorbing and measuring the quantity of desorbed fluid. In accordance with this invention, the adsorption is simultaneously carried out on all of the samples and thereafter the samples are seriatim subjected to a desorption step and the desorbed fluid is passed to a detector wherein the quantity of desorbed fluid is determined for each of the samples.

Still another embodiment of this invention resides in an apparatus for measuring the amount of fluid adsorbed by a plurality of samples which differs from the first defined apparatus in that the sample holding means are not arranged for movement between different chambers but rather are stationary in a chamber while the individual release is achieved by separate heating elements, with each sample holding means having one heating element associated therewith. Thus, an apparatus is provided in accordance with this embodiment which comprises an adsorption and desorption zone which has means for exposing a plurality of samples to a fluid. A detector is operatively connected to the adsorption and desorption zone. In the adsorption and desorption zone a plurality of sample holding means are provided for. For each sample holding means an individually controllable heating element is operatively connected to the sample holding means so that the individual sample in the individual sample holding means can be heated independently of all the other sample holding means and also without an unduly high rise of the temperature of any of the other samples. Housing means enclose the adsorption and desorption zone.

Correspondingly, a still further embodiment of this invention resides in a process for determining the quantity of a fluid adsorbed by each of a plurality of samples. This process comprises the steps of adsorbing, desorbing and measuring the quantity of desorbed fluid. In accordance with this embodiment of the invention the adsorption is simultaneously carried out on all of the samples and thereafter the samples are seriatim subjected to a heating step to achieve desorption by individually activating the heating element associated with the individual sample holding means containing the sample to be desorbed.

Further details and preferred embodiments, both for the apparatus and for the process of this invention will become apparent from the following description of the drawing.

A train of sample holders 58 thermally separated from each other by heat shield units 72 is moveably arranged in an elongated housing 71 having removable closure means (not shown) at one of its ends which allow the sample train to be inserted and removed from the housing 71. Surrounding the housing 71 are three units 36, 40 and 44. The section of the housing 71 arranged within unit 36 is a drying zone. Unit 36 is provided with heating means such as coil 38 for applying heating energy to the samples in order to dry them.

The portion of the housing 71 located within unit 44 constitutes the adsorbing zone. Unit 44 is provided with cooling means (not shown) which allow the cooling of the samples in the sample holders 58 to a low temperature. Advantageously this can be achieved by cooling the section of the housing 71 located within unit 44 to liquid nitrogen temperature.

The section of the housing located within unit 40 constitutes the desorbing zone. Unit 40 is provided with heating means (not shown) which allow heating of the sample to release the adsorbed fluid the quantity of which is representative of the surface area of the sample.

The transporting means for moving the sample train from unit 36 into unit 44 and seriatim back into and out of unit 40 is shown as a conveyor belt or wire 56 driven by pulleys 55. Care must be taken in this embodiment to avoid the entraining of any extraneous gas through the space through which the conveyor 56 passes into the housing 71.

The surface area determination of the plurality of samples in the plurality of sample holders 58 is carried out as follows. The entire train of sample holders 58 with the samples therein is placed into the drying zone, i.e. the portion of housing 71 contained in unit 36. The samples are heated in this unit 36 to remove essentially all of the water from the surface areas of the samples. Thereafter, the sample train by means of the conveyor 56 is moved into the adsorption section, i.e. that portion of the housing 71 that is located within unit 44. In the adsorption section, the samples are cooled to a low temperature. The samples are exposed to the flow of a carrier gas such as helium or hydrogen containing an adsorbing fluid such as nitrogen, oxygen, argon, carbon dioxide, propane or n-butane.

The samples are exposed to the carrier gas and the adsorbing fluid for a time sufficient to equilibrate the adsorption of the adsorbing fluid on the sample surfaces of all the samples. Then the first sample is moved from the adsorbing zone into the desorption zone, i.e. the portion of the housing 71 arranged within unit 40. In the desorption zone, the sample is heated to a temperature where essentially all the adsorbing fluid is released from the sample (desorbed) and removed with the flowing carrier gas through the detector 28 for measuring the quantity of desorbed fluid as will be described later. After essentially all the adsorbed fluid has been released from one sample this sample is removed from the desorbing zone and the next and still cold sample is introduced into this zone. The desorbing procedure is repeated until essentially all of the adsorbed fluid has been removed from that sample. This sequence is repeated until all of the samples have been measured. Thereafter, the sample train if desired can be replaced by another sample train and the sequence of steps described can be repeated.

The gas inlet valve 14 is connected to two or more nitrogen-containing gas streams 16 and 18 of differing compositions and is actuated by controller 10. The purpose of this embodiment of the invention is to allow one to automatically obtain data on the adsorption of nitrogen upon the solid sample material from nitrogen-containing gas streams with differing partial pressures of nitrogen. Such a capability will allow the practitioner to obtain potentially more reliable surface area measurements by having two separate sets of data points upon which to base calculations. A flow regulator 20 provides for constant flow of carrier gas from line 22 through the apparatus. Valve 14 allows switching from one stream 16 to the other stream 18 and vice versa. The gas stream comprising the carrier gas and the adsorbing fluid—in the following referred to as the gas stream— then flows through a dryer 24 and a fixed resistance 26. This fixed resistance can consist of a tube packed with crushed fire brick or molecular sieve material. This fixed resistance can be arranged anywhere downstream on the flow regulator 20 and upstream of the detector 28. The function of this fixed resistance 26 is to provide a pressure drop, for example of 10 psi, in the system which results in an increased sensitivity of the apparatus.

The gas stream then flows through one branch of the thermal conductivity detector, a unit well known in the art. This thermal conductivity detector is very sensitive to any change of composition of the gas flowing through this detector. In FIG. 1 the gas stream at 32 is divided into two gas streams 34 and 35 entering the housing 72 at the opposing ends thereof. The two gas streams flow from the opposing ends inside of a housing 71 to the desorption zone located in unit 40 and leave the housing 71 at the desorption zone entraining all the desorbed fluid from the sample.

The gas containing the desorbed fluid is passed through a delay volume 46 and a gas valve 52 to the detector 28. The delay volume 46 has the function to prevent any overly rapid changes in the flow rate of the gas stream through the detector which might be interpreted as composition changes by the sensitive detector 28. The gas valve 52 allows the calibration of the instrument as will be described later.

The gas stream containing desorbed fluid has a different composition, namely a higher concentration of adsorbing fluid then the gas stream that was not exposed to a desorption of a sample. The thermal conductivity of the gas is therefore changed and the corresponding signal from the detector is generated and transmitted to a recorder 50. The gas is finally passed through a pressure measuring device 47 and a back pressure regulator 48.

In the preferred embodiment of this invention, an automatic control device 10 is provided for. This automatic control device receives a signal responsive to the measured gas stream composition via line 75 and generates manipulating signals to operate a motor driving the pulleys 55 via line 73 and thus to advance the samples to the various locations. Furthermore, the control device 10 generates a manipulating signal to operate valve 14 and this manipulating signal is provided via line 74.

The calibration of the detector 28 which is located within a temperature stabilized zone 30 is done as follows. A defined volume 70 is filled with adsorbing gas at a well defined pressure. Valve 52 is then turned 180° so that the gas flow coming from delay volume 46 will entrain the defined quantity of adsorbing gas. The output signal generated by the detector 28 is therefore responsive to a known quantity of adsorbing gas and from another signal, the unknown quantity can therefore be calculated. Plotting detector signal versus time results in a peak or bell shaped curve and the area under this curve is proportional to the quantity of desorbed gas passed through the detector 28.

Increased accuracy and greater reliability of the measurements can be achieved when the measurement is repeated with a gas stream having a different partial pressure of the adsorbing fluid. This is done by switching valve 14 and allowing the other gas stream to flow through the system.

Instead of a thermal conductivity detector 28, other detectors suitable for measuring the quantity of a desorbed fluid in a gas stream can also be used. Thus, flame ionization detectors can be used in connection with a carbon containing gas as the adsorbed gas. Examples of such carbon containing gases are propane and n-butane.

The apparatus of this invention as shown in the drawing has a linear elongated housing 71 containing the drying zone, the adsorption zone and the desorption zone. It is also possible and contemplated within this invention to arrange these zones along a circle. Although it is preferred to arrange the desorbing zone between the adsorbing and the drying zones any other arrangement is also contemplated by this invention.

The apparatus of this invention allows the automatic measurement of surface areas of the plurality of samples. Controller device 10 can be designed in such a way as to subject the first sample to drying, adsorbing and desorbing, thereafter to subject the next sample to drying, adsorbing and desorbing and so forth. Alternatively, it is contemplated to simultaneously dry all the samples, to simultaneously have all the samples adsorb the adsorbing gas and then seriatim subject the samples to the desorption step, one at a time. The controller device 10 can be operated so that the desorption of the samples is carried out at a constant time for each sample. Another way of operating the control device 10 is to generate a signal via line 73 for advancing the samples only after the signal from recorder 50 via line 75 has indicated that the signal from detector 28 has returned to the base line, i.e. that no detectable quantity of desorbed fluid is present in the gas stream anymore. The calculation of the surface area from the amount of desorbed fluid is well known in the art. For example, the BET equation can be used for this purpose.

Preferably, in accordance with this invention the output signal of the detector 28 is used in a computer of which control device 10 may be a portion. This computer may both store the information, carry out the integration, provide the control signals and perform any logical operations for which it may be programmed.

Temperature ranges for the drying zone, the adsorbing zone, the desorbing zone and the detector unit 30 are dependent, of course, on the nature of the adsorbing fluid. Typical temperature ranges are given in the following table:

TABLE

| Zones | Temperature Range |
| --- | --- |
| Drying Zone | 100–300° C. |
| Adsorption Zone | −200–50° C. |
| Desorption Zone | 0–150° C. |
| Constant Temperature Zone 30 | 30–85° C. |

Another embodiment of this invention is shown in FIG. 2. In this embodiment, the fluid or gas stream is not split into two parallel streams which are reunited at the desorption zone as shown in FIG. 1, but rather the entire stream flows via conduit 42 into one end of the housing 71 and leaves the housing at the other end from where this gas stream flows via conduit 34 into the measuring unit 30. When the measurement is carried out according to this embodiment of the invention during the desorption step it is necessary to activate the heating means of drying zone 36 in order to prevent the desorbed gas (for instance, nitrogen) from the desorption zone from the sample, from being subsequently readsorbed by the solid samples in the drying zone which had previously been desorbed in the desorption zone.

In FIGS. 3 and 4 portions of the presently preferred transporting means are illustrated. Several sample containers 58 are connected in a train-like manner. At both ends of the train a magnet 60 is arranged (only 1 magnet is shown in FIG. 3). Adjacent to the housing 71 a conveyor belt 64 which can be driven via motor driven rollers 66 is provided for. On this conveyor belt, two magnets 62 (again only one is shown) are arranged. The distance between the two magnets 62 and the distance between the magnets 60 is the same. Furthermore, the distance between the magnets 60 and their arrangement is such that the train of containers 58 is in a completely extended location, i.e. without any slack. By moving the conveyor 64 the two magnets 60 are also moved and pull the sample containers or boats 58 along with them and into the desired positions.

FIG. 5 illustrates the embodiment of this invention wherein the individual sample holders are not moved from one zone into another zone but rather are arranged stationary during the adsorption and desorption and measurement steps. Cooling means are provided (not shown in the drawing) to cool the unit 105, both during the adsorbtion and during the individual desorbtion step. Valve 14 and measuring unit 30 are essentially identical to those described in connection with the previous embodiments and reference is therefore made to the description of these units above. The individual samples 103 are contained in individual sample holders 58 which are thermally insulated against each other. The individual sample holders 58 are provided with individual heater elements 101 such as electrical heaters in the bottom section 102 of the sample holder 58. Each individual heating element 101 is connected via conduit or cable to a switch 107 which is actuated from a control unit 10 and provides power from a power source 108 to the heating element 101 selected by the control unit 10 via switch 107. The individual sample holders 58 with their heating elements are mounted on a support 6 within the housing 105. The sample holders 58 with their heating elements 101 may conveniently be provided with plugs at the bottom which plug into outlets on the support 6. Thereby the individual sample holders 58 can be readily removed from the support 6. A door 106 is provided to allow removal of support 6 together with all the sample holders 58.

It is preferred to provide each of the sample holders 58 with highly thermally insulating walls surrounding both the sample 103 and the heating element 101. The heat generated by heating element 101 thus only reaches the sample 103 which is associated with the respective heating element and essentially no heat from one heating element 101 reaches the sample in the neighboring sample holder 58. In addition, it is preferred to arrange the flow of desorbing gas in such a way that it passes the sample holders 58 and correspondingly the samples contained therein "in parallel" rather than "in series" so that there is substantially no gas flow from one sample in one sample holder 58 to another sample 103 in another sample holder 58. By this arrangement, maximum accuracy will be assured. For this preferred embodiment, the inlet and outlet to the housing 105 would be in the bottom and the top of the housing rather than in the left and right upper side of the housing as shown in the drawing, FIG. 5.

During the operation of this embodiment of the invention, all samples are simultaneously subjected to the adsorption gases. Thereafter, each sample 103 is desorbed by activating the heating element 101 associated with the respective sample 103. Electrical heating of the samples 103 is presently preferred. The heating of each desorbed sample is preferably maintained while the subsequent sample is desorbed thereby avoiding significant re-adsorbtion.

Reasonable variations and modifications which will become apparent to those skilled in the art can be made in this invention without departing from the spirit and scope thereof.

I claim:

1. An apparatus for measuring the amount of a fluid adsorbed by each of a plurality of samples comprising
   (a) an adsorption and desorption zone provided with means for exposing the plurality of samples to said fluid,
   (b) a detector operatively connected to said adsorption and desorption zone and capable of detecting the fluid released from said sample and generating a signal representative of the quantity of said released fluid,
   (c) a plurality of sample holding means within said adsorption and desorption zone,
   (d) a plurality of individually controllable heating elements, each one sample holding means being associated with one of said heating elements such as to permit individual heating of each sample arranged in the respective sample holding means independently of the heating of all the other samples,
   (e) housing means enclosing said adsorption and desorption zone and separating said adsorption and desorption zone from uncontrolled contact with the surrounding atmosphere,
   (f) control means for activating each individual heating element in order to heat the sample associated with this heating element and to desorb said fluid from said sample.

2. Apparatus in accordance with claim 1 wherein a first conduit is operatively connected to said housing such as to provide a controllable connection between said adsorption and desorption zone and a source of carrier gas and adsorbing fluid and wherein a second conduit is operatively connected to said housing and to said detector.

3. Apparatus in accordance with claim 1 wherein said controller is operatively connected to said detector such as to seriatim activate the individual heating elements each activation being carried out after the concentration of the desorbed fluid has fallen below a given value and/or after the expiration of a given time period.

4. A process for determining the quantity of a fluid adsorbed by each of a plurality of samples comprising the following steps
   (a) introducing said plurality of samples in a plurality of sample holding means, each sample in an individual sample holding means, into a housing surrounding an adsorption and desorption zone and separating the adsorption and desorption zone and thus the samples in the sample holding means from uncontrolled contact with the surrounding atmosphere, said sample holding means being provided with individually actuated heating elements,
   (b) subjecting said samples at a low first temperature in the adsorption and desorption zone to said fluid for a time sufficient to achieve adsorption of said fluid on said samples,
   (c) heating one sample to effect desorption of said fluid of one sample while leaving the other samples essentially unchanged,
   (d) delivering the desorbed fluid to a detector,
   (e) generating a signal in said detector responsive to the quantity of fluid desorbed by the sample,
   (f) carrying out the desorption and signal generating steps seriatim on all of the samples.

5. A process in accordance with claim 4 wherein said samples are subjected to the contact of a carrier gas and an adsorbing fluid, wherein said carrier gas is selected from the group consisting of hydrogen and helium and wherein said adsorbing fluid is selected from the group consisting of nitrogen, oxygen, argon, carbon dioxide, propane and n-butane.

6. A process in accordance with claim 1 wherein said samples are dried prior to the adsorption step within said housing surrounding said adsorption and desorption zone.

7. A process in accordance with claim 6 wherein said drying is effected by heating said samples, which heating is carried out by actuating said individually controllable heating elements simultaneously or seriatim.

* * * * *